(12) United States Patent
Ranahan, II

(10) Patent No.: US 11,013,775 B2
(45) Date of Patent: May 25, 2021

(54) CHEMOTHERAPEUTIC COMPOUNDS, PRODUCTION METHODS AND APPARATUSES THEREFOR, AND METHODS OF CANCER TREATMENT

(71) Applicant: Oral Roberts University, Tulsa, OK (US)

(72) Inventor: William P. Ranahan, II, Tulsa, OK (US)

(73) Assignee: Oral Roberts University, Tulsa, OK (US)

( * ) Notice: Subject to any disclaimer, the term of this patent is extended or adjusted under 35 U.S.C. 154(b) by 482 days.

(21) Appl. No.: 15/814,068

(22) Filed: Nov. 15, 2017

(65) Prior Publication Data

US 2019/0142887 A1    May 16, 2019

(51) Int. Cl.
| | | |
|---|---|---|
| A61K 36/07 | (2006.01) | |
| A61K 9/00 | (2006.01) | |
| G01N 33/50 | (2006.01) | |
| A01G 18/00 | (2018.01) | |

(52) U.S. Cl.
CPC ............ *A61K 36/07* (2013.01); *A61K 9/0053* (2013.01); *G01N 33/5011* (2013.01); *A01G 18/00* (2018.02)

(58) Field of Classification Search
CPC ...... A61K 36/00; A61K 36/07; A61K 36/068; A61K 9/0053; A01G 18/00; G01N 33/5011
USPC .................................................. 424/195.15
See application file for complete search history.

(56) References Cited

U.S. PATENT DOCUMENTS

| | | | |
|---|---|---|---|
| 6,221,663 | B1 | 4/2001 | Bhatia et al. |
| 9,018,171 | B2* | 4/2015 | Ko .................... A61K 31/337 514/19.8 |
| 9,080,199 | B2 | 7/2015 | Palsson et al. |
| 2002/0164797 | A1 | 11/2002 | Martin et al. |
| 2003/0134329 | A1 | 7/2003 | Norman et al. |
| 2003/0170656 | A1 | 9/2003 | Cen et al. |
| 2006/0045887 | A1* | 3/2006 | Mahajna ............ A61K 36/07 424/195.15 |
| 2010/0255999 | A1 | 10/2010 | Mitsiades et al. |
| 2012/0309647 | A1 | 12/2012 | Collins et al. |

FOREIGN PATENT DOCUMENTS

| | | |
|---|---|---|
| JP | 4077399 | 4/2008 |
| KR | 100408011 | 12/2003 |
| WO | 2011035185 | 3/2011 |

OTHER PUBLICATIONS

Zhang et al. "Cell-cycle arrest and apoptosis induction in human breast carcinoma MCF-7 cells by carboxymethylated b-glucan from the mushroom sclerotia of Pleurotus tuber-regium" (Year: 2006).*
"Induction Of Diverse Secondary Metabolites In Aspergillus Fumigatus By Microbial Co-Culture" Mostafa E. Rateb ab, Irene Hallyburton c, Wael E. Houssen ad, Alan T. Bull e, Michael Goodfellow f, Rakesh Santhanam f,Marcel Jaspars a and Rainer Ebel. DOI: 10.1039/C3RA42378F (Paper) RSC Adv., 2013, 3, 14444-14450. Web. http://pubs.rsc.org/en/content/articlehtml/2013/ra/c3ra42378f.
"Co-Culture Systems And Technologies: Taking Synthetic Biology To The Next Level" Lisa Goers, Paul Freemont, Karen M. Polizzi. Published May 14, 2014.DOI: 10.1098/rsif.2014.0065. Web. http://rsif.royalsocietypublishing.org/content/11/96/20140065.short.
"Methodologies And Perspectives Of Proteomics Applied To Filamentous Fungi: From Sample Preparation To Secretome Analysis". Linda Bianco and Gaetano Perrotta. Web. http://www.mdpi.com/1422-0067/16/3/5803/htm . Int. J. Mol. Sci. 2015, 16(3), 5803-5829; doi:10.3390/ijms16035803.
"Transcription Profile Of Trichophyton Rubrum Conidia Grown On Keratin Reveals The Induction Of An Adhesin-Like Protein Gene With A Tandem Repeat Pattern". Tamires Aparecida Bitencourt, Claudia Macedo, Matheus Eloy Franco, Amanda Freire Assis, Tatiana Takahasi Komoto, Eliana Guedes Stehling, Rene Oliveira Beleboni, Iran Malavazi, Mozart Marius and Ana Lúcia Fachin. BMC Genomics201617:249. DOI: 10.1186/s12864-016-2567-8. Web. http://bmcgenomics.biomedcentral.com/articles/10.1186/s12864-016-2567-8.
Patel, Set al. Recent developments in mushrooms as anti-cancer therapeutics: a review. 3 Bioscience. Nov. 25, 2011, 2(1): pp. 1-15; abstract; URL<https://www.ncbi.nlm.nih.gov/pmc/articles/PMC3339609/>.
National Cancer Institute. Medicinal Mushrooms (PDQ®)-Health Professional Version. Oct. 6, 2017; URL<https://www.cancer.gov/about-cancer/treatment/cam/hp/mushrooms-pdq>.
PCT International Search Report and Written Opinion; PCT/US2018/059037; dated Nov. 2, 2018; US.

* cited by examiner

*Primary Examiner* — Aaron J Kosar
(74) *Attorney, Agent, or Firm* — Dennis D. Brown; Brown Patent Law, P.L.L.C.

(57) ABSTRACT

Methodologies and apparatuses are provided for producing new anti-cancer compounds and compositions by placing mushrooms or mushroom mycelia in contact with cancer cells or tissues and harvesting secretions produced by the mushrooms or mushroom mycelia which will destroy cancer cells without harming normal cells and tissues. The anti-cancer compounds are administered to humans or other mammals for cancer treatment.

40 Claims, 6 Drawing Sheets

CHEMOTHERAPEUTIC COMPOUNDS, PRODUCTION METHODS AND APPARATUSES THEREFOR, AND METHODS OF CANCER TREATMENT

FIELD OF THE INVENTION

The present invention relates to chemotherapeutic compounds and compositions, methods of and apparatuses for producing the chemotherapeutic compounds and compositions using mushrooms or mushroom mycelia, and methods of cancer treatment using the chemotherapeutic compounds and compositions.

BACKGROUND OF THE INVENTION

The medicinal properties of mushrooms have been known for thousands of years. China and India have used Reishi and Shiitake mushrooms for the general promotion of immune function and for cancer treatment while cultures in Eastern Europe have used mushrooms for gastrointestinal disorders, cancer, and asthma. Mushrooms have also been used for medicinal reasons throughout Mesoamerica for millennia. The United States has only recently begun to move beyond the exclusive use of mushrooms as food. The past 20 years has seen a great increase in the discovery of uses for mushrooms and mushroom derived compounds.

Some mushroom, extracts have been found to have beneficial anti-tumor, anti-diabetic, anti-viral, hypocholesterolemic, nephroprotective, or immunomodulatory effects when consumed. For example, when consumed, some mushrooms provide immunomodulatory peptides which, while being harmless to the patient, stimulate a robust immune response. This boost in immune response can be beneficial for standard chemotherapy regimens which leave patients in an immunocompromised state.

Although there are numerous published reports describing the purported anti-cancer benefits of certain mushroom extracts, these reports have not involved the engineering, capture, and testing of released compounds. Extraction procedures liberate the intracellular components of mushrooms with the hope that some of these extracts will be medically beneficial. In reality, however, most extraction components are not biologically useful for humans. Rather, the purpose of these internal components is to maintain the viability of the mushroom.

In nature, mushrooms serve to break down organic matter, returning it to a form suitable for plants. Mushrooms filter out toxic waste, protect trees from infection, and transport nutrients much like our cardiovascular system. Mushrooms also form symbiotic relationships with many trees and smaller plants, allowing for the extensive diversity found in tropical rainforests. Although, the topsoil of many rainforests is less than 6 inches deep, this soil is enough to support the diversity of the plant life above.

Mushrooms and other fungi cannot run away from predators and cannot produce their own food. Instead, they have elaborate chemical mechanisms for breaking down and absorbing the organic matter around them. Such mechanisms are the result of epigenetic processes occurring within the fungi wherein, in producing and secreting enzymes and/or other compounds for breaking down and absorbing the available organic material, the genes expressed by the fungi, and any modifications to those genes which may need to occur, are determined by the environment of the organism.

While the genome sequences of many mushrooms have been elucidated, science is far from understanding the regulatory mechanisms which govern their gene expression. Epigenetics is a well-established phenomenon whereby previously silent genes begin to be expressed following changes in the organism's environment. Mushrooms are eukaryotic multicellular organisms which employ a wide range of epigenetic regulators of gene expression. These regulatory mechanisms are not well understood but can have a dramatic impact on gene expression.

SUMMARY OF THE INVENTION

In the present invention, compounds or compositions which are secreted or otherwise released (i.e., not extracted) from mushrooms or mushroom mycelia are captured for use in treating cancers of all kinds which occur in humans or other mammals. These compounds or compositions are destructive of cancer cells and tissues but are not harmful to surrounding non-cancerous cells (e.g., normal breast epithelia). At least some of these compounds or compositions are produced in accordance with an inventive method wherein an environment for the mushrooms or mushroom mycelia is created and/or progressively changed to cause epigenetic changes in the gene expression of the mushrooms or mushroom mycelia such that the mushrooms or mushroom mycelia effectively adapt to fight cancer. In addition, the present invention provides devices which are well suited for interfacing the mushrooms or mushroom mycelia in contact with cancer cells, monitoring and analyzing the results obtained, and recovering the secreted compounds or compositions.

In one aspect, there is provided a method of producing agents that are selectively destructive of cancer cells or tissues wherein the method preferably comprises the step of exposing one or more mushrooms or mushroom mycelia to dead cancer cells to cause the one or more mushrooms or mushroom mycelia to release at least one compound or composition which breaks down the dead cancer cells.

In this method of producing agents that are selectively destructive of cancer cells or tissues, the step of exposing the one or more mushrooms or mushroom mycelia to the dead cancer cells preferably comprises serially passaging the one or more mushrooms or mushroom mycelia in or on a culture media wherein, in succeeding stages of the serial passaging, a nutrient content of the culture media is reduced and the dead cancer cells are added to the culture media in increasing amounts.

In another aspect, there is provided a method of producing agents that are selectively destructive for cancer cells or tissues wherein the method preferably comprises the step of interfacing one or more mushrooms or mushroom mycelia in contact with live cancer cells or tissues to cause the one or more mushrooms or mushroom mycelia to release at least one compound or composition which is destructive for the live cancer cells or tissues. In this method, it is also preferred that the live cancer cells or tissues which are interfaced with and contacted by the one or more mushrooms or mushroom mycelia be periodically replaced with fresh live cancer cells of tissues.

In another aspect, there is provided a method of producing agents that are selectively destructive for cancer cells or tissues wherein the method preferably comprises the steps of: (a) exposing one or more mushrooms or mushroom mycelia to dead cancer cells using a training procedure to produce and identify at least one trained mushroom or mushroom mycelia which has been trained by the training procedure to release at least one compound or composition which breaks down the dead cancer cells and (b) interfacing the trained mushroom or mushroom mycelia produced and identified in step (a) in contact with live cancer cells or tissues to cause the trained mushroom or mushroom mycelia to release at least one compound or composition which is destructive for the live cancer cells or tissues, wherein the compound or composition released by the trained mushroom or mushroom mycelia which is destructive for the live cancer cells or tissues in step (b) may be the same as or different from the compound or composition released by the trained mushroom or mushroom mycelia in step (a) which breaks down the dead cancer cells.

In this method of producing agents that are selectively destructive for cancer cells or tissues, the training procedure of step (a) preferably comprises serially passaging each of the one or more mushrooms or mushroom mycelia in or on a culture media wherein, in succeeding stages of the serial passaging, a nutrient content of the culture media is reduced and the dead cancer cells are added to the culture media in increasing amounts. In step (b), the live cancer cells or tissues which are interfaced with and contacted by the trained mushroom or mushroom mycelia will preferably be periodically replaced with fresh live cancer cells or tissues of the same type.

In another aspect, there is provided a method of producing agents that are selectively destructive for cancer cells or tissues wherein the method preferably comprises the steps of: (a) exposing one or more mushrooms or mushroom mycelia to dead cancer cells using a training procedure to identify at least one trainable type of mushroom or mushroom mycelia which can be trained to release a compound or composition which breaks down the dead cancer cells and (b) interfacing the trainable type of mushroom or mushroom mycelia identified in step (a) in contact with live cancer cells or tissues to cause the trainable type of mushroom or mushroom mycelia to release at least one compound or composition which is destructive for the live cancer cells or tissues, wherein the compound or composition released by the trainable type of mushroom or mushroom mycelia which is destructive for the live cancer cells or tissues in step (b) may be the same as or different from the compound or composition referenced in step (a) which breaks down the dead cancer cells.

In this method of producing agents that are selectively destructive of cancer cells or tissues, the training procedure of step (a) preferably comprises serially passaging each of the one or more mushrooms or mushroom mycelia in or on a culture media wherein, in succeeding stages of the serial passaging, a nutrient content of the culture media is reduced and the dead cancer cells are added to the culture media in increasing amounts. In step (b), the live cancer cells or tissues which are interfaced with and contacted by the trainable type of mushroom or mushroom mycelia will preferably be periodically replaced with fresh live cancer cells or tissues.

In another aspect, there is provided a treatment method for a human or other mammal having a cancer of the same type as the dead cancer cells or live cancer cells or tissues used in any of the methods described above wherein the treatment method preferably comprises administering to the human or other mammal a chemotherapeutic agent comprising a compound or composition which is, or is the same as (e.g., is a synthetically produced version of), the compound or composition released by the mushroom or mushroom mycelia used in the method which was effective for breaking down the dead cancer cells or was destructive for the live cancer cells or tissues in question.

In another aspect, there is provided a method of identifying agents that are selectively destructive of cancer cells and tissues wherein the method preferably comprises the steps of: (a) recovering a compound or composition secreted by a mushroom or mushroom mycelia; (b) adding the compound or composition to a culture comprising cancer cells and normal cells; and (c) monitoring the culture to identify morphological changes indicating a destruction of at least some of the cancer cells by the compound or composition without substantially harming the normal cells.

In this method, the compound or composition is preferably recovered in step (a) by sterilizing by filtration a media having the secreted material therein and then evaporating the media to produce a powder compound or composition. In step (b), the powder compound or composition is preferably added to the culture comprising the cancer cells and normal cells by suspending the powder product in distilled water to form a suspension and then adding the suspension directly to the culture. In step (c), the culture is preferably monitored to identify morphological changes by protein analysis and mRNA analysis of samples taken from the culture.

In another aspect, there is provided an apparatus for interfacing one or more mushrooms or mushroom mycelia in contact with cancer cells or tissues comprising: (a) a first piece having a top opening and an interior for receiving a dish having the cancer cells or tissues therein; (b) a second piece having a lower portion which is receivable in the interior of the first piece through the top opening of the first piece, the lower portion having a bottom end; and (c) an interface plate on top of which the one or more mushrooms or mushroom mycelia will be placed. The interface plate is provided at the bottom end of the lower portion of the second piece so that when the lower portion of the second piece is received in the interior of the first piece, the cancer cells or tissues in the dish will be beneath the interface plate. The interface plate has a plurality of openings therethrough for interfacing the one or more mushrooms or mushroom mycelia with the cancer cells or tissues beneath the interface plate.

In another aspect, there is provided an apparatus for interfacing one or more mycorrhizal mushrooms or mushroom mycelia living on or in the roots of a plant with cancer cells or tissues. The apparatus preferably comprises: (a) a first piece having a top opening and an interior for receiving a dish having the cancer cells or tissues therein; (b) a second piece which is receivable in the interior of the first piece through the top opening of the first piece, the second piece having an interior and the interior of the second piece having a bottom end; and (c) an interface plate on top of which the roots of the plant will rest. The interface plate is provided at the bottom end of the interior of the second piece so that when the second piece is received in the interior of the first piece, the cancer cells or tissues will be beneath the interface plate. The interface plate has a plurality of openings therethrough for interfacing the roots of the plant with the cancer cells or tissues beneath the interface plate.

This apparatus for use with mycorrhizal mushrooms or mushroom mycelia living on or in the roots of a plant also preferably comprises a third piece which is receivable on top of the second piece. The third piece preferably has a top opening through which the plant will extend for receiving light, the top opening of the third piece being smaller than a cross-sectional area of the interior of the second piece at the interface plate. In addition it is preferred that the third piece include an interior conduit structure through which the plant will extend. The interior conduit structure preferably (i) extends downwardly within the interior of the third piece from the top opening of the third piece and (ii) has a bottom opening which is smaller than a bottom opening of the third piece. Most preferably, the bottom opening of the interior conduit structure will be smaller than the top opening of the third piece.

Further aspects, features, and advantages of the present invention will be apparent to those in the art upon examining the accompanying drawings and upon reading the following Detailed Description of the Preferred Embodiments.

DETAILED DESCRIPTION OF TOE PREFERRED EMBODIMENTS

Figure 1:
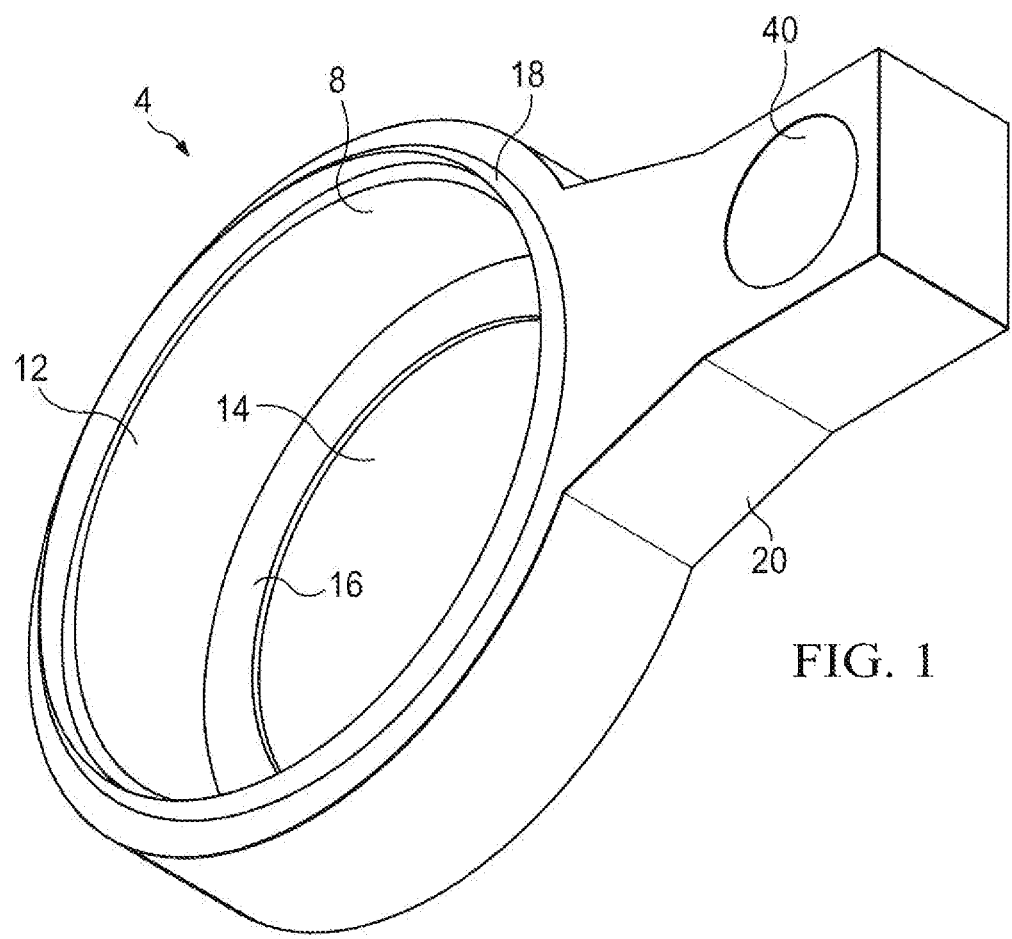
FIG. 1 is a perspective view of a bottom piece 4 of a first embodiment of an apparatus provided by the present invention for interfacing mushrooms or mushroom mycelia in contact with live cancer cells or tissues.

The present invention provides various preferred methodologies for producing and/or capturing compounds or compositions released form mushrooms or mushroom mycelia which are destructive for cancer cells or tissues but are not harmful to surrounding non-cancerous cells.

One of the inventive methodologies is a dead cell methodology in which the mushrooms or mushroom mycelia are adapted to produce anti-cancer compounds through nutrient deprivation and exposure to dead cancer cells. Another of the inventive methodologies is a live cell methodology in which the mushrooms or mushroom mycelia are adapted to produce anti-cancer compounds by interfacing with live cancer cells. Another of the inventive methodologies is a first combination methodology in which mushrooms or mushroom mycelia which have been trained to break down dead cancer cells using the inventive dead cell methodology are then interfaced with live cancer cells in accordance with the inventive live cell methodology. Another of the inventive methodologies is a second combination methodology in which fresh mushrooms or mushroom mycelia of the type previously identified as being trainable for breaking down dead cancer cells are interfaced with live cancer cells. Another of the inventive methodologies is a "wild-type" methodology in which compounds secreted by wild-type mushrooms in or on standard cultures or other cultures are recovered and tested for anti-cancer properties.

As used herein and in the claims, the term "destructive for cancer cells or tissues" means that the secretions, fractions, compounds, or compositions in question cause the cells of the cancer to die and/or rupture or otherwise cause the cancer cells or tissues to be rendered non-viable.

The Dead Cell Methodology

In the dead cell methodology of the present invention, agents that are selectively destructive of cancer cells and tissues are produced by exposing one or more mushrooms or mushroom mycelia to dead cancer cells to train the mushrooms or mushroom mycelia to release one or more new compounds or compositions which break down the dead cancer cells. By way of example, but not by way of limitation, the dead cell methodology can be used for developing anti-cancer agents which are effective against cell lines derived from "Triple Negative" Er-/PR-/Her2- breast cancer, as well as human sarcoma cell lines derived from patients with Ewing's Sarcoma.

In the dead cell methodology, the mushrooms or mushroom mycelia are preferably (a) grown in or on a culture media containing standard nutrients and then (b) used (or "trained") in a serial passaging procedure wherein, in each succeeding stage of the procedure, the one or more mushrooms or mushroom mycelia are cultured on a media wherein the standard nutrient content of the media has been reduced and the amount of dead cancer cells added to the media has been increased. The serial passaging procedure is preferably continued at least until it is observed or otherwise confirmed that the mushroom(s) or mushroom mycelia is/are secreting compounds which are breaking down the dead cancer cells. Most preferably, the serial passaging procedure will be continued until all of the standard nutrients have been replaced and the trained mushroom(s) or mycelium is/are surviving exclusively on the dead cancer cells.

Due to the saprophytic nature of mushrooms, they are able to live off dead and decaying matter. Consequently, most of the mushrooms and mushroom mycelia used in the present invention will adapt more rapidly to break down dead cancer cells than to kill or break down live cancer cells of the same type. However, the anti-cancer compounds or compositions produced by the mushrooms or mycelia for breaking down the dead cancer cells will typically be the same as those produced on live cancer cells.

The culture media used in the dead cell methodology can be any media which is effective for exposing the mushrooms or mushroom mycelia to the dead cancer cells such that, as the serial passaging procedure continues, the mushrooms or mushroom mycelia will be trained to produce and secrete one or more compounds or compositions which are effective for breaking down the dead cancer cells. Examples of culture media suitable for use in the first methodology include, but are not limited to, solid agar and solid agar supplemented with various substrates from the mushroom's native environment, such as sawdust from a species of tree preferred by that mushroom.

The media used in the dead cell methodology will preferably be a solid agar media supplemented with nutrients in accordance with standard mushroom or mycelia culturing procedures. In at least some cases (e.g., when using *Hericium erinaceus*) the agar media will also preferably have sterile alder chips and/or sawdust added thereto.

Examples of mushroom genera suitable for use in any of the inventive methodologies described herein for producing anti-cancer compounds or compositions include, but are not limited to, the genera: *Trametes; Hericium; Ganoderma; Lentinula; Grifola; Fomitopsis; Inontus; Phellinus; Fomes; Piptoporus; Pleurotus; Agaricus; Clitocybe; Antrodia;*

*Cordyceps; Xerocomus; Calvatia; Schiziphyllum; Flammulina; Suillus; Inocybe; Funlia; Lactarius; Albatrellus; Russula;* and/or *Fomes.*

Examples of mushrooms or mycelia preferred for use in any of the inventive methodologies described herein for producing anti-cancer compounds or compositions when exposed to or interfaced with dead and/or live breast cancer cells include, but are not limited to: *Trametes versicolor; Hericium erinaceus; Ganoderma applanatum; Gandoderma lucidum; Lentinula edodes; Grifola frondosa; Fomitopsis pinicola; Inontus obliquus; Phellinus igniarius/tremulae; Fomes fomentarius;* and/or *Piptoporus betulinus.*

Examples of mushrooms or mycelia preferred for use in any of the inventive methodologies described herein when producing anti-cancer compounds or compositions for basal type adenocarcinomas include, but are not limited to: *Trametes versicolor; Hericium erinaceus;* and/or *Ganoderma applanatum.*

Examples of mushrooms or mycelia preferred for use in any of the inventive methodologies described herein when producing anti-cancer compounds or compositions for sarcoma cancer include but are not limited to: *Ganoderma applanatum; Fomitopsis pinicola; Inontus obliquus; Fomes fomentarius;* and/or *Piptoporus betulinus.*

Alternatively, the one or more mushrooms or mushroom mycelia used in any of the inventive methodologies described herein for producing compounds or compositions which are destructive for cancer cells can be one or more mycorrhizal mushrooms or mycelia living on or in the roots of a plant. Examples of mycorrhizal fungi or mycelia suitable for use in any of the methodologies of the present invention include, but are not limited to: *Glomus aggregatum; Glomus erinaceuse; Glomus intraradices; Glomus mosseae; Glomus clarum; Glomus deserticola; Glomus monosporous; Gigaspora margarita;* and/or *Para Glomus brasilianum.*

In the inventive methodologies, the use of mycorrhizal mushrooms or mycelia living on or in the roots of a plant to produce anti-cancer compounds and compositions involves an epigenetic change in regulation of gene expression of the fungi or mycelia via symbiosis. In the symbiotic relationship, the plant produces glucose, by photosynthesis, which it shares with the mycorrhizal mushroom or mycelia. The mushroom or mycelia in turn breaks down the organic matter close to the roots of the plant to more efficiently provide beneficial nutrients and minerals. Mycelia thus connected to the plant root system continue to branch out, greatly increasing the potential area of nutrient absorption.

In the dead cell methodology of the present invention, when using mycorrhizal mushrooms or mycelia, the roots of the plant on or in which the mycorrhizal mushrooms or mycelia are living are preferably placed in a soil or in a hydroponic solution to which the dead cancer cells have been added. Thus, the one or more mycorrhizal fungi or mycelia are exposed to the dead cancer cells together with the roots on or in which the mycorrhizal fungi or mycelia are living to cause the mycorrhizal fungi or mycelia to release the compound or composition which breaks down the dead cancer cells.

Examples of hydoponic systems suitable for use in the present invention include, but are not limited to: (a) the AEROGARDEN systems available from Miracle-Gro and (b) a system comprising plant grow lights, a water tank, water agitators, water aerators, soluble plant supplements, pH meters, ppm meters, and thermometers.

Although other types of plants can also be used, the plants used in the inventive methodologies described herein when producing anti-cancer compounds or compositions from mycorrhizal mushrooms or mycelia will preferably be plants which, themselves, are known to produce compounds having beneficial anti-cancer properties of one sort or another. Examples include, but are not limited to: green tea plants which produce polyphenols or other antioxidants; litchi leaf plants which produce flavonoids; and oilseed plants which produce Brassinosteroids.

Although other methods can also be used, selected mycorrhizal fungi will preferably be combined with a desired plant by growing the plant, from seeds, in a hydroponic system and then adding the mycorrhizal fungi to the water once the roots of the plant are developed. The development of a successful symbiotic relationship between the fungi and the plant can then be measured by the enhanced growth of the plant, and/or visual inspection of the roots.

When using mycorrhizal mushrooms or mycelia in any of the methodologies, the fungi can be tested individually or a blend of mycorrhizal fungi can be added to the plant and then tested individually if an efficacy against dead and/or live cancer cells is observed.

The Live Cell Methodology

In the live cell methodology of the present invention, agents that are selectively destructive for cancer cells and tissues are produced by interfacing one or more mushrooms or mushroom mycelia in contact with live cancer cells or tissues to train the one or more mushrooms or mushroom mycelia to release at least one new compound or composition which is destructive for the live cancer cells or tissues. By way of example, but not by way of limitation, the live cell methodology can be used tor developing anti-cancer agents which are effective against "Triple Negative" Er-/PR-/Her2-breast cancer, as well as human sarcoma cell lines derived from patients with Ewing's Sarcoma.

In the live cell methodology, the live cancer cells or tissues which are in contact with the mushrooms or mushroom mycelia are preferably grown in standard tissue culture conditions and are preferably replaced periodically with fresh live cancer cells or tissues of the same type. The periodic replacement of the live cancer cells or tissues with fresh cells and tissues is preferably performed approximately every 3 to 4 days and preferably continues at least until it is observed or otherwise determined that the mushroom(s) or mycelia has/have adapted to produce secretions which are killing the live cancer cells or tissues. Most preferably, the cancer cells are periodically replaced and maintained in contact with the one or more mushrooms or mushroom mycelia until phenotypic changes are observed in the cancer cells or tissues, with respect to control populations of non-tumorigenic cells or tissues.

Alternatively, or in addition, live cancer cells or tissues can be periodically replaced as part of a serial passaging or training procedure, similar to the procedure described above, wherein in each succeeding stage, the nutrient content of the culture media supporting the live cancer cells or tissues is reduced and the amount of live cancer cells or tissue in the media is increased.

By way of example, but not by way of limitation, the one or more mushrooms or mushroom mycelia used in the inventive live cancer methodology can be any of the non-mycorrhizal or mycorrhizal mushrooms or mushroom mycelia identified above.

Figure 2:
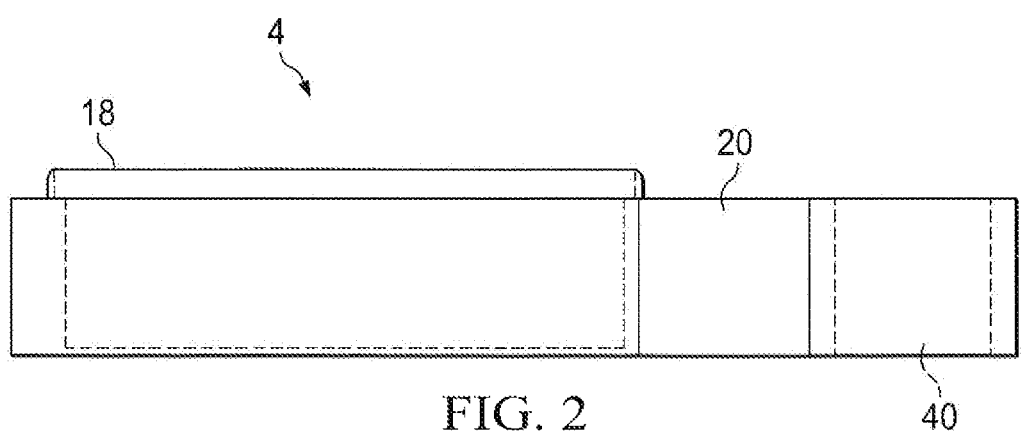
FIG. 2 is an elevational side view of the bottom piece 4.
Figure 3:
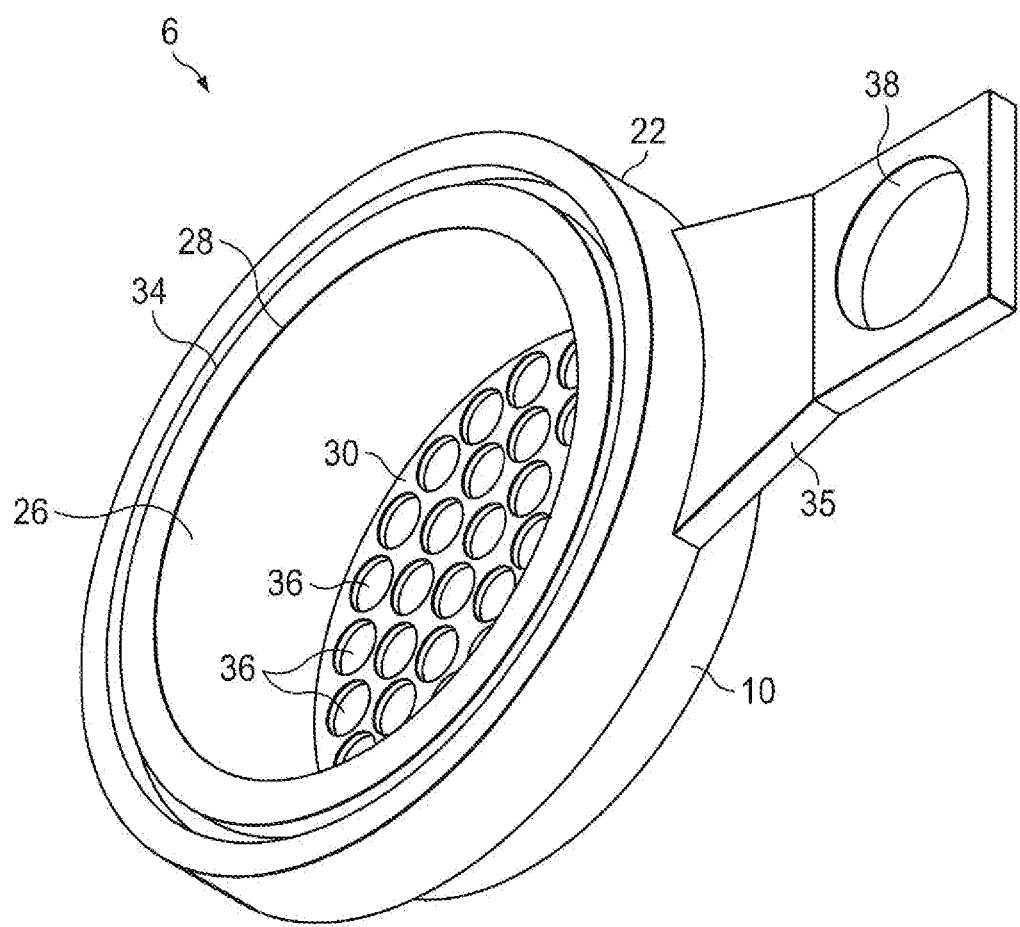
FIG. 3 is a perspective view of a top piece 6 of the first embodiment of the inventive apparatus.
Figure 4:
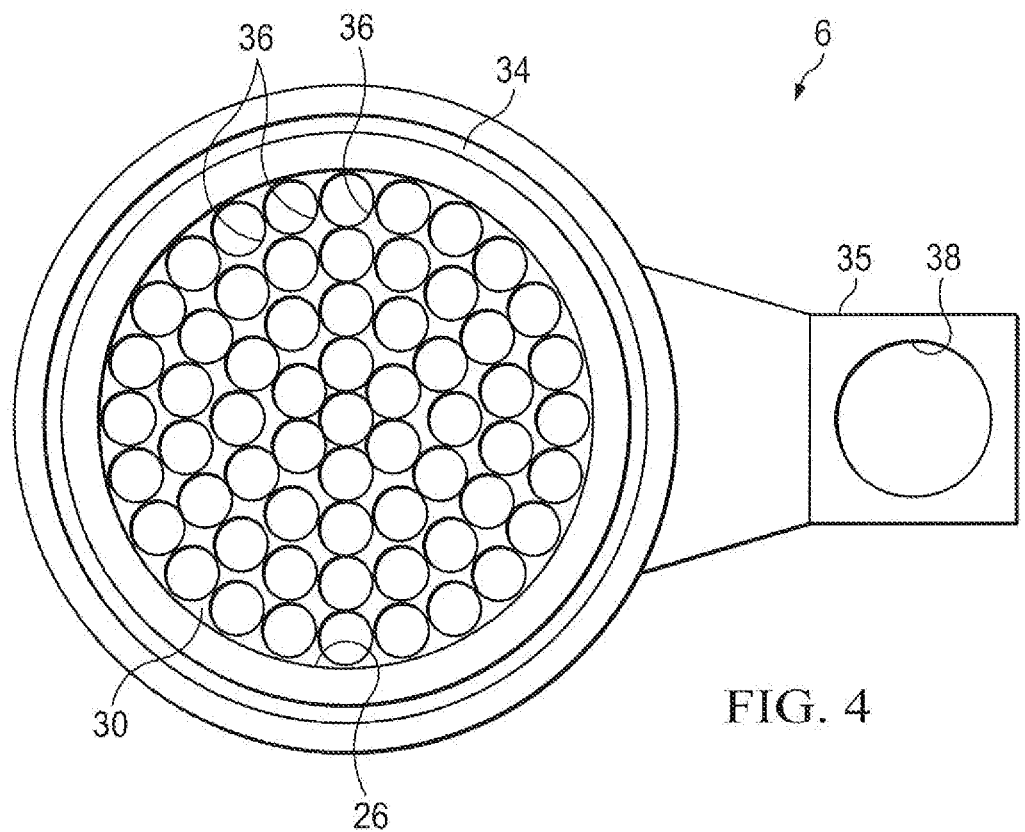
FIG. 4 is a plan view of the top piece 6.
Figure 5:
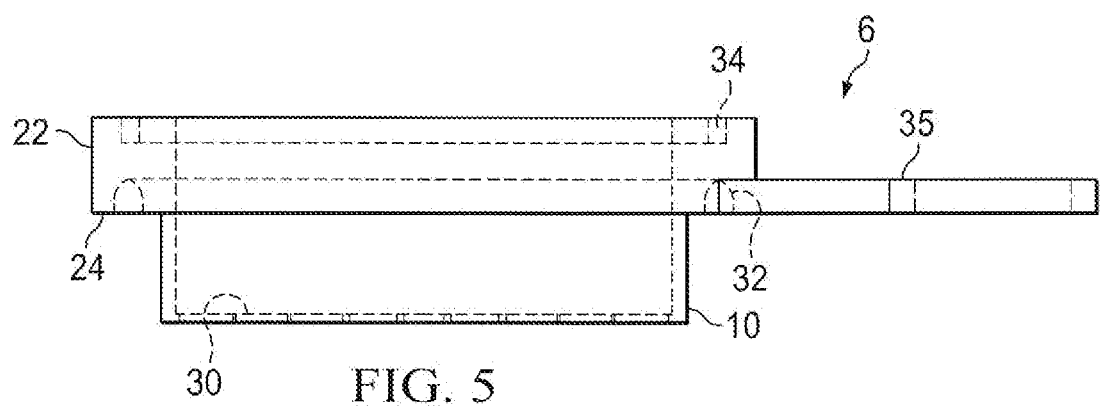
FIG. 5 is an elevational side view of the top piece 6.

An embodiment of an apparatus provided by the present invention for interfacing one or more non-mycorrhizal mushrooms or mushroom mycelia in contact with live cancer cells or tissues is illustrated in FIGS. 1-5. The apparatus comprises (a) a bottom piece 4 for receiving an open tissue culture dish (lid removed) having cancer cells or tissues living therein in a culture media and (b) a top piece 6 which holds the one or more mushrooms or mushroom mycelia and which is insertable into the bottom piece 4 for placing the mushroom(s) or mycelia in contact with the cancer cells in the open tissue culture dish.

The bottom piece 4 of the inventive apparatus preferably comprises: a cylindrical interior 8 having a depth which is sufficient for holding the tissue culture dish and for receiving a cylindrical insertable lower portion 10 of the top piece 6; an upper opening 12 through which the tissue culture dish and the insertable lower portion 10 of the top piece 6 are inserted and removed; an open lower end 14 which allows the contents of the tissue culture dish to be visually observed and analyzed to some degree (e.g., using a tissue culture microscope) without having to disassemble the inventive apparatus and/or disrupt or interfere with the seal or integrity of the culturing system or process; an inwardly projecting radial lip 16 which surrounds the open lower end 14 of the bottom piece 4 for retaining and supporting the tissue culture dish in the bottom piece 4; an upwardly projecting sealing ridge 18 which surrounds the upper opening 12; and a radially extending exterior arm 20.

The top piece 6 of the inventive apparatus preferably comprises: an upper portion 22 having a larger outside diameter than the insertable lower portion 10 such that an exterior, downwardly facing, radial shoulder 24 is formed around the upper end of the insertable lower portion 10; a cylindrical interior 26 which extends from an upper opening 28 of the upper portion 22 to an interface plate 30 which is formed or installed in the lower end of the insertable lower portion 10; a circular, downwardly facing bottom groove 32 formed in the downwardly facing radial shoulder 24 of the top piece 6 for receiving the upwardly projecting sealing ridge 18 of the lower piece 4 when the lower portion 10 of the top piece 6 is inserted into the bottom piece 4; a circular, upwardly facing groove 34 formed around the upper opening 28 of the top piece 6 for receiving the lid of the tissue culture dish to thereby seal the apparatus when in use in order to protect the system from contamination; and an exterior arm 35 which extends radially outward from the upper portion 22 of the top piece 6.

When in use, the interface plate 30 in the bottom of the top piece 6 supports a mat of the mushroom or mycelia material which rests on top of the interface plate 30. The vertical height of the insertable portion 10 of the top piece 6 will preferably be such that, when inserted into the bottom piece 4, the interface plate 30 in the lower end of the insertable portion 10 will contact and rest on the top of the media in the tissue culture dish. In addition, the interface plate 30 includes a plurality of circular or other openings 36 which preferably extend over substantially the entire area of the plate 30. Through these openings 36, the mushroom(s) or mycelia on top of the plate 30 are allowed to interface with and contact the live cancer cells or tissues in the tissue culture dish beneath.

To further facilitate the interfacial contact between the mushroom(s) or mycelia and the live cancer cells or tissues in the tissue culture dish, the thickness of the interface plate 30 will preferably be less than 7 mm and will more preferably be less than 5 mm. In addition, the plurality of openings 36 extending over tire interface plate 30 will preferably have a diameter in the range of from about 3 mm to about 5 mm (more preferably about 4 mm) and will preferably be grouped such that the center to center distance between the openings 36 is in the range of from about 7 mm to about 8 mm (more preferably about 7.5 mm) depending upon the size of the openings 36.

As viewed from above, the radial arm 36 extending outwardly from the exterior of the top piece 6 of the inventive apparatus is preferably of the same shape and size as the radial arm 20 extending from the exterior of the bottom piece 4. In addition, the radial arms 36 and 20 of the top and bottom pieces 6 and 4 preferably have circular openings 38 and 40 of the same size extending therethrough such that, when the top and bottom pieces 6 and 4 are coupled for use, the radial arms 36 and 20 and the openings 38 and 40 extending therethrough will be in vertical alignment. The radial arms 36 and 20 (a) provide a more secure gripping means when moving the system to ensure that the seal and internal integrity of the system are maintained, (b) assist in setting up a more standardized and repeatable system by minimizing exposure of the cells to potential contamination sources, and (c) allow for attachment of the apparatus to a central vertical rod which would enable the rotation or addition of alternative interfaces with the same tissue culture dish.

Figure 6:
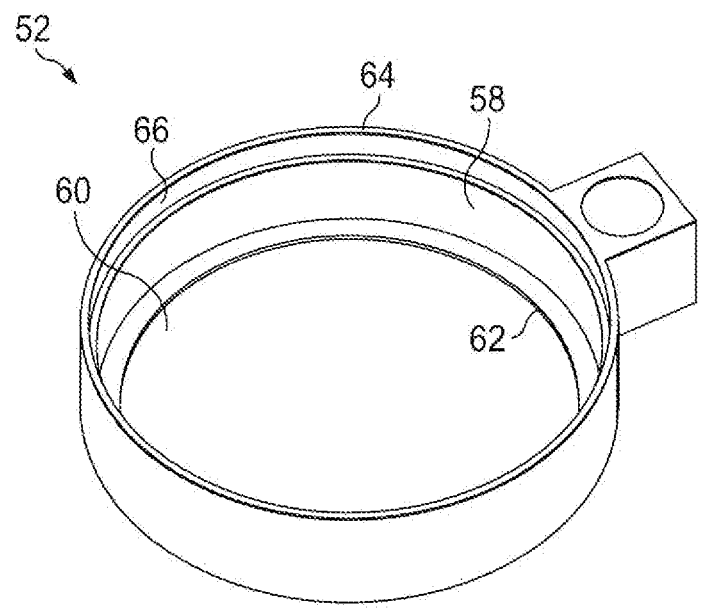
FIG. 6 is a perspective view of a bottom piece 52 of a second embodiment of the apparatus provided by the present invention for interfacing live cancer cells or tissues with mycorrhizal mushrooms or mushroom mycelia living on or in the roots of a plant.
Figure 7:
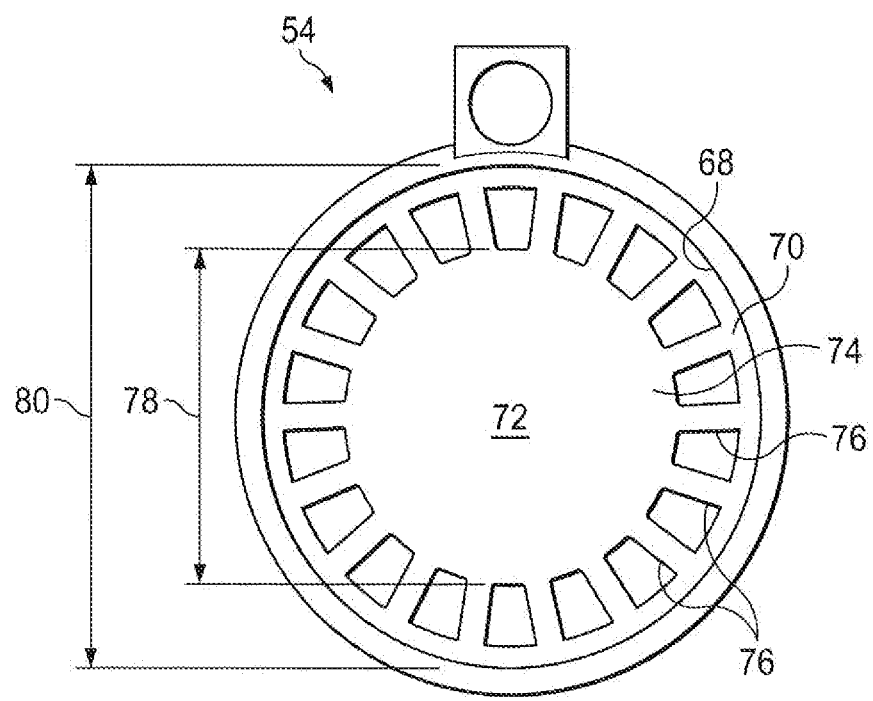
FIG. 7 is a plan view of a middle piece 54 of the inventive second apparatus.
Figure 8:
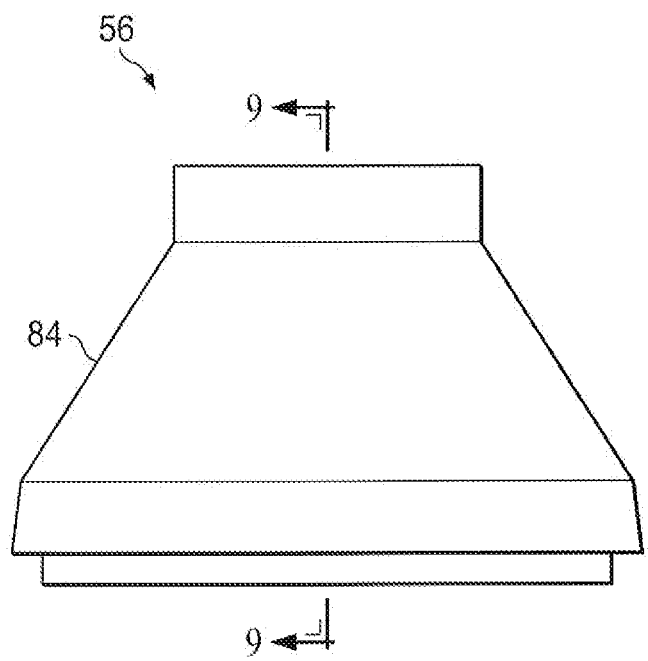
FIG. 8 is an elevational side view of a top piece 56 of the inventive second apparatus.
Figure 9:
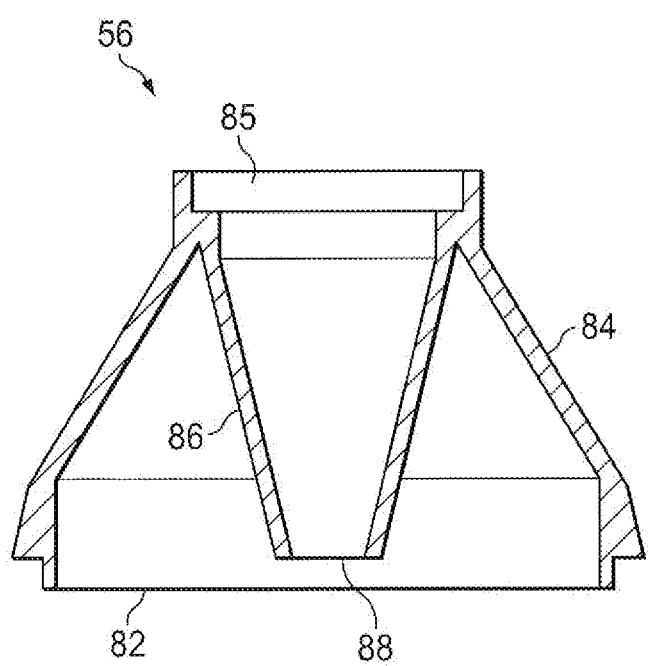
FIG. 9 is a cutaway elevational side view of the top piece 56.
Figure 10:
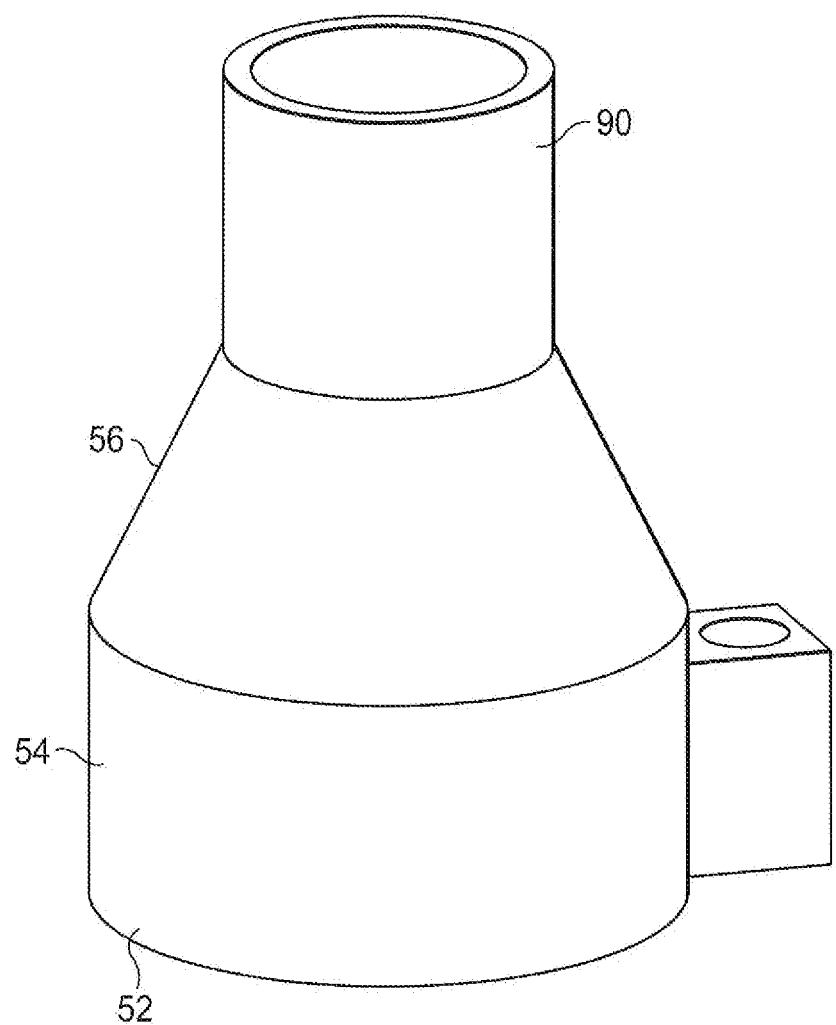
FIG. 10 is an elevational side view of the inventive second apparatus, as assembled, with an extension piece 90 placed on the top thereof for providing additional support for the stem or body of the plant.

A second embodiment of the inventive apparatus is illustrated in FIGS. 6-10. Although similar to the first apparatus, the second apparatus is preferred for use when performing the inventive live cell methodology using one or more mycorrhizal mushrooms or mushroom mycelia which are living on or in the roots of a plant. The inventive second apparatus is configured for both (a) supporting and providing light to the plant while (b) interfacing the roots of the plant in contact with cancer cells or tissues living in a dark environment. The inventive second apparatus comprises a bottom piece 52, a middle piece 54 which is receivable in the bottom piece 52, and a top piece 56 which is receivable on the middle piece 54.

The bottom piece 52 preferably comprises: a cylindrical interior 58; an open lower end 60; an inwardly extending radial lip 62 which surrounds the open lower end 60 of the bottom piece 52 for retaining and supporting the tissue culture dish containing the live cancer cells or tissues; and an open upper end 64 through which the tissue culture dish is received and removed. The diameter of a short upper portion 66 of the cylindrical interior 58 of the bottom piece 52 is larger than the diameter of the remainder of the cylindrical interior 58 in order to allow the lid of the tissue culture dish to be placed on the top of the dish whenever the bottom piece 52 is removed for studying the contents of the tissue culture dish under a microscope or for other purposes.

The middle piece 54 of the inventive second apparatus preferably comprises: a cylindrical interior 68; an open upper end 70; and an interface plate 72 at the lower end of the cylindrical interior 68 on which the roots of the plant will rest. When in use, the middle piece 54 preferably extends downwardly into the bottom piece 52 to a distance such that the interface plate 72 will contact and rest on the top of the media in the tissue culture dish. The interface plate 72 preferably comprises a large, closed central portion 74 which is surrounded by a series of open slots 76. The closed central portion 74 of the interface, plate 72 will support the excess roots of the plant as the plant grows and will also protect the live cancer cells or tissues in the tissue culture dish by effectively blocking substantially any light which happens to enter the inventive apparatus through the specially designed top piece 56. The diameter 78 of the closed central portion 74 of the interface plate 72 is preferably in the range of from about 70% to about 80% of the total cross-sectional diameter 80 of the cylindrical interior 68 of the middle piece 54.

The top piece 56 of the inventive second apparatus preferably comprises: an open lower end 82; an outer conical wall 84 which converges inwardly as the outer conical wall 84 extends upwardly to the upper portion of the top piece 56; an upper opening 85 which is smaller than the open lower end 82 and is smaller than the internal cross-sectional diameter 80 of the middle piece 54; an internal conduit structure (preferably a funnel-shaped structure) 86 which converges inwardly as the internal funnel structure 86 extends downwardly from the upper opening 85 to near the open lower end 82 of the top piece 56; and a lower opening 88 provided in the bottom of the internal funnel structure 86 which is preferably smaller than the upper opening 85 of the top piece 56.

When the inventive second apparatus is in use, the stem or body of the plant will extend upwardly through the internal funnel structure 86 so that the plant will project from the upper opening 85 of the top piece 56 for receiving light. The reduced size of the lower and upper openings 88 and 85 of the internal funnel structure 86 help to support the plant in a manner so as to prevent the plant from wilting and thus having to expend energy in supporting itself. In addition, the downwardly converging shape of the internal funnel structure 86 operates to focus any light entering the upper opening 85 onto a very small central area on the closed central portion 74 of the interface plate 72 so that the entering light is substantially blocked from reaching the live cancer cells or tissues in the tissue culture dish beneath. Light is also blocked from passing through the small lower opening 88 of the internal funnel structure 86, at least to a substantial degree, by the plant itself.

The inventive second apparatus can be readily placed in a typical incubator which will also preferably have an internal light source installed therein which will be positioned above the plant. As the height of the plant increases, one or more extension pieces 90 can be connected to the upper opening 85 of the inventive apparatus 50 to provide additional support as needed to prevent wilting.

The First Combination Methodology

In the first combination methodology of the present invention, agents that are selectively destructive for cancer cells and tissues are produced by the steps of: (a) exposing one or more mushrooms or mushroom mycelia to dead cancer cells using a training procedure in accordance with the dead cell methodology described above to produce and identity at least one trained mushroom or mushroom mycelia which has been trained by the training procedure to release at least one compound or composition which breaks down the dead cancer cells and then (b) using the live cell methodology describe above to interface the mushroom(s) or mushroom mycelia trained in step (a) in contact with live cancer cells or tissues to cause the trained mushroom(s) or mushroom mycelia to release at least one compound or composition which is destructive for the live cancer cells or tissues.

In the first combination procedure, the compound(s) or composition(s) released by the trained mushroom(s) or mushroom mycelia which is/are destructive of the live cancer cells or tissues in step (b) may be the same as or may be different from the compound(s) or composition(s) released by the trained mushroom(s) or mushroom mycelia in step (a) which break down the dead cancer cells.

By way of example, but not by way of limitation, the first combination methodology can be used for developing new anti-cancer agents which are effective against "Triple Negative" Er-/PR-/Her2-breast cancer, as well as human sarcoma cell lines derived from patients with Ewing's Sarcoma.

By way of example, but not by way of limitation, the one or more mushrooms or mushroom mycelia used in the inventive first combination methodology can be any of the non-mycorrhizal or mycorrhizal mushrooms or mushroom mycelia identified above.

The Second Combination Methodology

In the second combination methodology of the present invention, agents that are selectively destructive of cancer cells and tissues are produced by the steps of: (a) exposing one or more mushrooms or mushroom mycelia to dead cancer cells using a training procedure in accordance with the dead cell methodology described above to produce and identify at least one trained mushroom or mushroom mycelia which has been trained by the training procedure to release at least one compound or composition which breaks down the dead cancer cells and then (b) using the live cell methodology describe above to interface one or more fresh mushrooms or mushroom mycelia, of the same type identified as being trainable in step (a), in contact with live cancer cells or tissues to cause the trainable mushroom(s) or mushroom mycelia to release at least one compound or composition which is destructive of the live cancer cells or tissues.

In the second combination procedure, the compound(s) or composition(s) released by the trainable mushroom(s) or mushroom mycelia which is/are destructive of the live cancer cells or tissues in step (b) may be the same as or may be different from the compound(s) or composition(s) released by same type of mushrooms or mushroom mycelia in step (a) which broke down the dead cancer cells.

By way of example, but not by way of limitation, the second combination methodology can be used for developing new anti-cancer agents which are effective against "Triple Negative" Er-/PR-/Her2-breast cancer, as well as human sarcoma cell lines derived from patients with Ewing's Sarcoma.

By way of example, but not by way of limitation, the one or more mushrooms or mushroom mycelia used in the inventive second combination methodology can be any of the non-mycorrhizal or mycorrhizal mushrooms or mushroom mycelia identified above.

The Wild-Type Methodology

In the "wild-type" methodology, secretions from one or more non-trained mushrooms or mushroom mycelia, preferably living on standard types of media, are captured and then tested for anti-cancer properties. By way of example, but not by way of limitation, the one or more mushrooms or mushroom mycelia used in the inventive "wild-type" methodology can be any of the non-mycorrhizal or mycorrhizal mushrooms or mushroom mycelia identified above. In the case of mycorrhizal mycelia, the mycorrhizal fungi can be added to the roots of any selected plant using the procedure described above. Alternatively, the mycorrhizal fungi may be used in combination with a plant to which the mycorrhizal mushroom(s) or mushroom mycelia is/are already coupled.

Harvesting the Anti-Cancer Compounds or Compositions

In each of the methodologies described above, the secretions released by the one or more mushrooms or mushroom mycelia which are determined to be destructive for cancer cells or tissues or to have other anti-cancer properties are preferably harvested in a liquid media for further separation, fractionation, identification, testing, synthetic replication, direct use for cancer treatment, and/or other purposes. If a liquid media was used when interfacing the mushrooms or mushroom mycelia with the cancer cells or tissues, this same liquid media can be harvested directly for recovering the anti-cancer secretions.

On the other hand, in any of the inventive methodologies described above wherein the mushrooms or mushroom mycelia are interfaced with or otherwise contacted by dead or live cancer cells or tissues in a solid media, a liquid media for recovering the secreted material can be added to and then separated from the system. Examples of liquid media suitable for use in recovering the anti-cancer secretions include, but are not limited to: a reduced serum media such as Opti-MEM, DMEM, or double distilled sterile water.

The process of adding the liquid media to the system to recover the anti-cancer secretions produced by the mushrooms or mushroom mycelia will preferably involve: aseptic transfer of the liquid media to the mycelia (followed by a 24 hour incubation at 37 degrees Celsius). Subsequently, the procedure for separating the liquid media from the system will preferably involve aspiration of the media into a syringe followed by filter sterilization.

The recovery of the anti-cancer secretions in the liquid media preferably also comprises the steps of: sterilizing the harvested liquid media composition by passing the harvested fluid through one or a series of microfilters; evaporating the liquid to leave a dry powder composition; and then suspending the recovered powder in distilled water. An amount of the suspension can then be applied to a culture which preferably contains either live cancer cells or tissues or normal cells or tissues and the culture can be monitored to identify morphological changes indicating a destruction of the cancer cells or tissues without substantially harming the normal cells of tissues. By way of example, but not by way of limitation, the culture can be monitored to identity morphological changes by protein and mRNA analyses of samples taken from the culture.

Alternatively, or in addition, the liquid media containing secretions showing anti-cancer activity can be purified by microfiltration and or other means and then further processed by: fractionating the fluid to separate the fluid into multiple fractions; testing one or more or all of the fractions individually to determine if the fraction(s) is/are destructive for live cancer cells or tissues; and also optionally identifying individual compounds in one or more of the fractions and then recovering and testing one or more of the identified compounds to determine if the identified compound(s) is/are destructive of live cancer cell's or tissues.

Examples of fractionation proceedings which can be used to separate the fluid into distinguishable fractions include High Performance Liquid Chromatography and Fast Performance Liquid Chromatography. Examples of procedures which can be used to identify individual compounds within the fractions or within the fluid as a whole include: Gas Chromatography Mass Spectrometry, Tandem Liquid Chromatography Mass Spectrometry, or a sequence of Nuclear Magnetic Resonance and Infrared Spectral readings.

Treatment Methods for Humans and Other Mammals

In the inventive treatment method, a human or other mammal having a cancer of the same type or closely related to the dead and/or live cancer cells or tissues used in any of the inventive methodologies discussed above can be treated by administering to the human or other mammal a chemotherapuutic agent comprising a compound or composition which is, or is a synthetically produced or otherwise derived compound or composition which is the same as, the compound or composition released by the one or more mushrooms or mushroom mycelia used in the inventive methodology which was determined to be destructive for the cancer in question. As used herein and in the claims in this context, the term "closely related to" the dead and/or live cells or tissues tested means that both cellular morphology and genome expressions patterns would be very similar between the tumor cells and their respective cell lines.

In the inventive treatment method, the chemotherapuutic agent comprising the inventive anti-cancer compound or composition will preferably be orally administered to the patient or mammal. However, other suitable methods for administering the inventive anti-cancer compound or composition to the patient or mammal include, but are not limited to, subcutanious injection into the site of the tumor.

The inventive methodologies described above can be used for producing compounds and compositions which will be effective for treating all types of breast-cancer and other cancers. Examples include but are not limited to: basal type adenocarcinomas; sarcoma; bladder cancers; colon and rectral cancers; endometrial cancers; renal cell, renal, pelvis, and other kidney cancers; all types of leukemia; bronchus and other lung cancers; melanoma; non-Hodgkin lymphoma; pancreatic cancer; prostate cancer; and thyroid cancer.

EXAMPLE

Mushrooms (e.g., mycelial plug spawn or sterile rice inoculated with mycelia) are purchased as pure cultured mycelia growing on various plant-based supports. The mycelia are then transplanted to a variety of agar media such as the following to determine optimal growth conditions.

Malt Extract, Yeast Agar (MYA or MYPA) comprising: 1 L of water; 20 g agar agar; 20 g barley malt sugar; 2 g yeast; and 1 g peptone.

Potato, Dextrose, Yeast Agar (PDYA or PDYPA) comprising: 1 L water; 300 g of potato broth; 20 g agar; 10 g dextrose; 2 g yeast; and 1 g peptone.

Cornmeal, Yeast, Glucose Agar (CMYA) comprising: 1 L of water; 20 g agar agar; 10 g cornmeal; 5 g malt or glucose; and 1 g yeast.

Oatmeal, Malt, Yeast Enriched Agar (OMYA) comprising: 1 L of water; 80 g instant oatmeal; 20 g agar agar; 10 g malt sugar; and 2 g yeast.

Dog Food Agar (DFA) comprising: 1 L of water; 20 g dry dog food; and 20 g agar agar.

For *H. erinaceus* and other mycelia as needed, sterile sawdust is also added to the media to facilitate growth.

The agar media are prepared and poured into petri dishes by: mixing the ingredients of the media in a 1 L bottle; autoclaving the media on a 15 minute wet cycle (leave the cap loose); putting the media bottle into a 55° C. water bath: at 55° C. pipetting ampicillin into the media (1 μl per mL, 1000×); mixing the ingredients; in a sterile hood, laying the petri dishes with the lids half open; pouring the media into the petri dishes about half way; waiting for the media to harden; and storing in a refrigerator at 4° C.

Each of the mycelia are then added to one of the media plates and cultured by: taking a wooden plug spawn, for example, from the initial mycelium container and placing it into a media agar plate; letting the mycelium run and form a complete sheath on the surface of the agar dish at room temp (7-10 days may be required); passaging the mushroom by taking a scalpel or inoculation loop and cutting a 1 square centimeter piece of mycelium on the outer edge of the plate; transferring to a new media agar plate; and labeling the passage number, date, mushroom type, and agar type (leave at room temp). For long term storage, test tubes containing media agar are inoculated and store in a refrigerator at 4° C.

The mycelia are then directly interfaced with cancer cells to detect potential anti-cancer secretions. The interfacing procedure involves: plating out a desired cancer cell line with 4 million cells in 100 mm dishes with media appropriate to the cell line; incubating the cells overnight at 37° C. with humidity and $CO_2$; in a sterile chemical fume hood, transferring a 5-10 cm cut from the mycelial mat to the interface plate; transferring the interface plate to the 60 mm dish, covering and incubating overnight as above; monitoring the cancer cells for changes in morphology or signs of apoptosis; testing a range of media for capture of mycelial secretions; filter-sterilizing media containing mycelial secretions; and reducing the filter sterilized media to a powder and suspending in distilled water.

The mushroom secretions are harvested by: pipetting 20 mLs of Opti-MEM/DMEM/ddH$_2$O/MEM onto the mycelium in a sterile hood; incubating for 48 hours at 37° C.; filter sterilizing with a 0.45 microfilter and a 0.22 microfilter; pipetting the sterilized product into a 15 or 50 mL falcon tube depending upon the amount of product collected; and storing at 4° C.

Tissue samples are then harvested for molecular analysis to determine the mechanism of mycelial secretion action. Preferred protocols include: RNA Prep (phenol-chloroform extraction); cDNA Synthesis (iScript Reverse Transcription Supermix for RT-qPCR); RT-qPCR (SsoAdvanced Universal SYBR Green Supermix); Western Blot; and Cell cytotoxicity assays.

Thus, the present invention is well adapted to carry out the objectives and attain the ends and advantages mentioned above as well as those inherent therein. While presently preferred embodiments and steps have been described for purposes of this disclosure, the invention is not limited in its application to the details of the preferred embodiments and steps. Numerous changes and modifications will be apparent to those in the art. Such changes and modifications are encompassed within this invention as defined by the claims. In addition, unless expressly stated, the phraseology and terminology employed herein are for the purpose of description and not of limitation.

What is claimed is:

1. A method of producing a compound or composition which is selectively destructive for cancer cells or tissues, the method comprising the steps of:
   a) culturing one or more living mushrooms or mushroom mycelia in contact with dead cancer cells to produce and identify at least one trained living mushroom or mushroom mycelium which undergoes an epigenetic change in gene expression when in contact with the dead cancer cells to produce and release at least one compound or composition which is observed or otherwise confirmed to break down the dead cancer cells for absorption by the trained living mushroom or mushroom mycelium and then
   b) culturing the trained living mushroom or mushroom mycelium produced and identified in step (a) in a system in which the trained living mushroom or mushroom mycelium is in contact with live cancer cells or tissues to cause the trained living mushroom or mushroom mycelium to produce and release at least one compound or composition which is destructive for the live cancer cells or tissues, wherein the compound or composition produced and released by the trained living mushroom or mushroom mycelium which is destructive for the live cancer cells or tissues in step (b) may be the same as or different from the compound or composition produced and released by the trained living mushroom or mushroom mycelium in step (a) which breaks down the dead cancer cells.

2. The method of claim 1 wherein, in step (a), each of the one or more living mushrooms or mushroom mycelia are cultured in or on a culture media using a serial passaging procedure in which a nutrient content of the culture media is reduced and the dead cancer cells are added to the culture media in increasing amounts.

3. The method of claim 1 wherein, in step (b), the trained living mushroom or mushroom mycelium is cultured in or on a culture media using a procedure in which the live cancer cells or tissues are periodically replaced with fresh live cancer cells or tissues of the same type.

4. The method of claim 1 further comprising the step of harvesting from the system the compound or composition produced and released by the trained living mushroom or mushroom mycelium in step (b) which is destructive for the live cancer cells or tissues.

5. The method of claim 1 wherein the one or more living mushrooms or mushroom mycelia are one or more living mycorrhizal fungi or mycelia which are living on or in the roots of a plant and wherein, in step (a), the one or more living mycorrhizal fungi or mycelia are cultured, together with the roots on or in which the mycorrhizal fungi or mycelia are living, in contact with the dead cancer cells.

6. The compound or composition produced and released by the trained living mushroom or mushroom mycelium in step (b) of claim 1 which is destructive for the live cancer cells or tissues.

7. A treatment method for a human or other mammal having a cancer of the same type as, or closely related to, the live cancer cells or tissues of claim 6, the treatment method comprising administering to the human or other mammal the compound or composition of claim 6.

8. The treatment method of claim 7 wherein the compound or composition is orally administered to the human or other mammal.

9. A method of producing a compound or composition which is selectively destructive for cancer cells or tissues, the method comprising the steps of:
   a) culturing one or more living mushrooms or mushroom mycelia in contact with dead cancer cells to identify at least one trainable living mushroom or mushroom mycelium of a type which undergoes an epigenetic change in gene expression when in contact with the dead cancer cells to produce and release a compound or composition which is observed or otherwise confirmed to break down the dead cancer cells for absorption by the trainable living mushroom or mushroom mycelium and then
   b) culturing a trainable living mushroom or mushroom mycelium of the type identified in step (a) in a system in which the trainable living mushroom or mushroom mycelium of the type identified in step (a) is in contact with live cancer cells or tissues to cause the trainable living mushroom or mushroom mycelium of the type identified in step (a) to undergo an epigenetic change in gene expression when in contact with the live cancer cells or tissues to produce and release at least one compound or composition which is destructive for the live cancer cells or tissues, wherein the compound or composition released by the trainable living mushroom or mushroom mycelium of the type identified in step (a) which is destructive for the live cancer cells or tissues in step (b) may be the same as or different from the compound or composition referenced in step (a) which breaks down the dead cancer cells.

10. The method of claim 9 wherein, in step (a), each of the one or more living mushrooms or mushroom mycelia are cultured in or on a culture media using a serial passaging procedure in which a nutrient content of the culture media is reduced and the dead cancer cells are added to the culture media in increasing amounts.

11. The method of claim 9 wherein, in step (b), the trainable living mushroom or mushroom mycelium of the type identified in step (a) is cultured in or on a culture media using a procedure in which the live cancer cells or tissues are periodically replaced with fresh live cancer cells or tissues.

12. The method of claim 9 further comprising the step of harvesting from the system the compound or composition produced and released in step (b), by the trainable mushroom or mushroom mycelium of the type identified in step (a), which is destructive for the live cancer cells or tissues.

13. The method of claim 9 wherein the one or more living mushrooms or mushroom mycelia are one or more living mycorrhizal fungi or mycelia which are living on or in the roots of a plant and wherein, in step (a), the one or more living mycorrhizal fungi or mvcelia are cultured, together with the roots on or in which the mycorrhizal fungi or mycelia are living, in contact with the dead cancer cells.

14. The compound or composition produced and released in step (b) of claim 9, by the trainable living mushroom or mushroom mycelium of the type identified in step (a), which is selectively destructive for the live cancer cells or tissues.

15. A treatment method for a human or other mammal having a cancer of the same type as, or closely related to, the live cancer cells or tissues of claim 14, the treatment method comprising administering to the human or other mammal the compound or composition of claim 14.

16. The treatment method of claim 15 wherein the compound or composition is orally administered to the human or other mammal.

17. A method of producing a compound or composition which is selectively destructive for cancer cells or tissues, the method comprising the step of culturing a living mushroom or mushroom mycelium in a system in which the living mushroom or mushroom mycelium is in contact with live cancer cells or tissues to cause the living mushroom or mushroom mycelium to undergo an epigenetic change in gene expression to produce and release at least one compound or composition which is destructive for the live cancer cells or tissues.

18. The method of claim 17 wherein, in the step of culturing, the living mushroom or mushroom mycelium is cultured in or on a culture media using a procedure in which the live cancer cells or tissues are periodically replaced with fresh live cancer cells or tissues.

19. The method of claim 17 further comprising the step of harvesting from the system the compound or composition produced and released by the living-mushroom or mushroom mycelium which is destructive for the live cancer cells or tissues.

20. The method of claim 17 wherein the living mushroom or mushroom mycelium is cultured in contact with the live cancer cells or tissues by placing the living mushroom or mushroom mycelium on an interface plate having apertures provided therethrough and placing the interface plate in contact with a media below the interface plate in which the live cancer cells or tissues are living.

21. The method of claim 17 wherein the living mushroom or mushroom mycelium is selected from the genera: *Trametes; Hericium; Ganoderma; Lentinula; Grifola; Fomitopsis; Inontus; Phellinus; Fomes; Piptoporus; Pleurotus; Agaricus; Clitocybe; Antrodia; Cordyceps; Xerocomus; Calvatia; Schiziphyllum; Flammulina; Suillus; Inocybe; Funlia; Lactarius; Albatrellus; Russula*; and/or *Fomes*.

22. The method of claim 17 wherein the live cancer cells or tissues are breast cancer cells or tissues and the living mushroom or mushroom mycelium is selected from: *Trametes versicolor; Hericium erinaceus; Ganoderma applanatum; Gandoderma lucidum; Lentinula edodes; Grifola frondosa; Fomitopsis pinicola; Inontus obliquus; Phellinus igniarius/tremulae; Fomes fomentarius*; and/or *Piptoporus betulinus*.

23. The method of claim 22 wherein the breast cancer cells or tissues are basal type adenocarcinomas.

24. The method of claim 23 wherein the living mushroom or mushroom mycelium is selected from: *Trametes versicolor; Hericium erinaceus*; and/or *Ganoderma applanatum*.

25. The method of claim 17 wherein the live cancer cells or tissues are sarcoma cancer cells or tissues and the living mushroom or mushroom mycelium is selected from: *Ganoderma applanatum; Fomitopsis pinicola; Inontus obliquus; Fomes fomentarius*; and/or *Piptoporus betulinus*.

26. The method of claim 17 wherein the living mushroom or mushroom mycelium is a living mycorrhizal fungi or mycelium which is living on or in the roots of a plant and wherein, in the step of culturing, the living mycorrhizal fungi or mycelium is cultured, together with the roots on or in which the mycorrhizal fungi or mycelium is living, in contact with the live cancer cells or tissues.

27. The method of claim 26 wherein the living mycorrhizal fungi or mycelium is selected from: *Glomus aggregatum; Glomus erinaceuse; Glomus intraradices; Glomus mosseae; Glomus clarum; Glomus deserticola; Glomus monosporous; Gigaspora margarita*; and/or *Para Glomus brasilianum*.

28. The method of claim 26 wherein the living mycorrhizal fungi or mycelium is cultured in contact with the live cancer cells or tissues by placing the roots of the plant on an interface plate having apertures surrounding a central solid portion of the interface plate and placing the interface plate in contact with a media below the interface plate in which the live cancer cells or tissues are living.

29. A treatment method for a human or other mammal having a cancer of the same type as, or closely related to, the live cancer cells or tissues of claim 17, the treatment method comprising administering to the human or other mammal the compound or composition produced and released by the living mushroom or mushroom mycelium in the method of claim 17 which is selectively destructive for the live cancer cells or tissues.

30. The treatment method of claim 29 wherein the compound or composition is orally administered to the human or other mammal.

31. The treatment method of claim 29 wherein the live cancer cells or tissues are breast cancer cells or tissues, the human or other mammal has a breast cancer of the same type as, or closely related to, the live cancer cells or tissues, and the living mushroom or mushroom mycelium is selected from: *Trametes versicolor; Hericium erinaceus; Ganoderma applanatum; Gandoderma lucidum; Lentinula edodes; Grifola frondosa; Fomitopsis pinicola; Inontus obliquus; Phellinus igniarius/tremulae; Fomes fomentarius*; and/or *Piptoporus betulinus*.

32. The treatment method of claim 29 wherein the live cancer cells or tissues are adenocarcinoma basal cancer cells or tissues, the human or other mammal has a adenocarcinoma basal cell cancer of the same type as, or closely related to, the live cancer cells or tissues, and the living mushroom or mushroom mycelium is selected from: *Trametes versicolor; Hericium erinaceus*; and/or *Ganoderma applanatum.*

33. The treatment method of claim 29 wherein the live cancer cells or tissues are sarcoma cancer cells or tissues, the human or other mammal has a sarcoma cancer of the same type as, or closely related to, the live cancer cells or tissues, and the living mushroom or mushroom mycelium is selected from *Ganoderma applanatum; Fomitopsis pinicola; Inontus obliquus; Fomes fomentarius*; and/or *Piptoporus betulinus.*

34. A method of producing agents that are selectively destructive for cancer cells or tissues, the method comprising the steps of:
   a) exposing one or more mushrooms or mushroom mycelia to dead cancer cells using a training procedure to produce and identify at least one trained mushroom or mushroom mycelia which has been trained by the training procedure to release at least one compound or composition which breaks down the dead cancer cells and
   b) interfacing the trained mushroom or mushroom mycelia produced and identified in step (a) in contact with live cancer cells or tissues to cause the trained mushroom or mushroom mycelia to release at least one compound or composition which is destructive for the live cancer cells or tissues, wherein the compound or composition released by the trained mushroom or mushroom mycelia which is destructive for the live cancer cells or tissues in step (b) may be the same as or different from the compound or composition released by the trained mushroom or mushroom mycelia in step (a) which breaks down the dead cancer cells,
   the training procedure comprising serially passaging each of the one or more mushrooms or mushroom mycelia in or on a culture media wherein, in succeeding stages of the serial passaging, a nutrient content of the culture media is reduced and the dead cancer cells are added to the culture media in increasing amounts.

35. A method of producing agents that are selectively destructive for cancer cells or tissues, the method comprising the steps of:
   a) exposing one or more mushrooms or mushroom mycelia to dead cancer cells using a training procedure to identify at least one trainable type of mushroom or mushroom mycelia which can be trained to release a compound or composition which breaks down the dead cancer cells and
   b) interfacing the trainable type of mushroom or mushroom mycelia identified in step (a) in contact with live cancer cells or tissues to cause the trainable type of mushroom or mushroom mycelia to release at least one compound or composition which is destructive for the live cancer cells or tissues, wherein the compound or composition released by the trainable type of mushroom or mushroom mycelia which is destructive for the live cancer cells or tissues in step (b) may be the same as or different from the compound or composition referenced in step (a) which breaks down the dead cancer cells,
   the training procedure comprising serially passaging each of the one or more mushrooms or mushroom mycelia in or on a culture media wherein, in succeeding stages of the serial passaging, a nutrient content of the culture media is reduced and the dead cancer cells are added to the culture media in increasing amounts.

36. A method of producing agents that are selectively destructive for cancer cells or tissues, the method comprising the steps of:
   a) exposing one or more mushrooms or mushroom mycelia to dead cancer cells using a training procedure to identify at least one trainable type of mushroom or mushroom mycelia which can be trained to release a compound or composition which breaks down the dead cancer cells and
   b) interfacing the trainable type of mushroom or mushroom mycelia identified in step (a) in contact with live cancer cells or tissues to cause the trainable type of mushroom or mushroom mycelia to release at least one compound or composition which is destructive for the live cancer cells or tissues, wherein the compound or composition released by the trainable type of mushroom or mushroom mycelia which is destructive for the live cancer cells or tissues in step (b) may be the same as or different from the compound or composition referenced in step (a) which breaks down the dead cancer cells,
   wherein the one or more mushrooms or mushroom mycelia are one or more mycorrhizal fungi or mycelia living on or in the roots of a plant and wherein, in the step of exposing, the one or more mycorrhizal fungi or mycelia are exposed to the dead cancer cells together with the roots on or in which the mycorrhizal fungi or mycelia are living.

37. A method of producing agents that are selectively destructive for cancer cells or tissues, the method comprising the step of interfacing one or more mushrooms or mushroom mycelia in contact with live cancer cells or tissues to cause the one or more mushrooms or mushroom mycelia to release at least one compound or composition which is destructive for the live cancer cells or tissues, wherein the live cancer cells or tissues which are interfaced with and contacted by the one or more mushrooms or mushroom mycelia are periodically replaced with fresh live cancer cells or tissues.

38. A method of producing agents that are selectively destructive for cancer cells or tissues, the method comprising the step of interfacing one or more mushrooms or mushroom mycelia in contact with live cancer cells or tissues to cause the one or more mushrooms or mushroom mycelia to release at least one compound or composition which is destructive for the live cancer cells or tissues, wherein the one or more mushrooms or mushroom mycelia are one or more mycorrhizal fungi or mycelia living on or in the roots of a plant and wherein, in the step of interfacing, the one or more mycorrhizal fungi or mycelia are interfaced in contact with the live cancer cells or tissues together with the roots on or in which the mycorrhizal fungi or mycelia are living.

39. The method of claim 38 wherein the one or more mycorrhizal fungi or mycelia are selected from: *Glomus aggregatum; Glomus erinaceuse; Glomus intraradices; Glomus mosseae; Glomus clarum; Glomus deserticola; Glomus monosporous; Gigaspora margarita*; and/or *Para Glomus brasilianum.*

40. The method of claim 38 wherein the one or more mycorrhizal fungi or mycelia are interfaced in contact with the live cancer cells or tissues by placing the roots of the plant on an interface plate having apertures surrounding a central solid portion of the interface plate and placing the interface plate in contact with a media below the interface plate in which the live cancer cells or tissues are living.

* * * * *